United States Patent [19]

Stack et al.

[11] Patent Number: 5,554,368

[45] Date of Patent: Sep. 10, 1996

[54] PSEUDOMONAS SYRINGAE ATCC 55389 AND USE THEREOF FOR INHIBITING MICROBIAL DECAY ON FRUIT

[75] Inventors: James P. Stack, Amherst; Steven N. Jeffers, Rutland, both of Mass.; Baruch Sneh, Rehovot, Israel; Teresa S. Wright, Worcester, Mass.

[73] Assignee: EcoScience Corporation, Northboro, Mass.

[21] Appl. No.: 162,533

[22] Filed: Dec. 3, 1993

[51] Int. Cl.$^6$ .............................. A01N 63/00; C12N 1/20
[52] U.S. Cl. .................................. 424/93.47; 435/253.3; 435/874
[58] Field of Search ............................ 435/253.3, 874; 424/93 N, 93.47

[56] References Cited

U.S. PATENT DOCUMENTS

| | | | |
|---|---|---|---|
| 3,155,585 | 11/1964 | De Vay | 167/65 |
| 4,377,571 | 3/1983 | Strobel | 424/93 |
| 5,232,850 | 8/1993 | Casida, Jr. | 435/253.3 |
| 5,270,059 | 12/1993 | Janisiewicz et al. | 424/93 N |

OTHER PUBLICATIONS

Chemical Patents Index, Documentation Abstracts Journal, Abstract 91–192885/26 "Biological Post–Harvest Rot Control in Apples and Pears—Uses *Pseudomonas Strain* from Apple Leaves" (Published May 1991).

Janisiewicz, W. J., et al., "Control of Storage Rots on Various Pear Cultivars with a Saprophytic Strain of *Pseudomonas syringae*," *Plant Dis.* 76:555–560 (1992).

Janisiewicz, W. J., et al., "Nutritional Enhancement of Biocontrol of Blue Mold on Apples," *Phytopathology* 82(11):1364–1370 (1992).

Janisiewicz, W. J., et al., "Biological Control of Blue Mold and Gray Mold on Apple and Pear with *Pseudomonas cepacia*," *Phytopathology* 78(12):1697–1700 (1988).

Janisiewicz, W. J., et al., "Nutritional Enhancement of Biocontrol of Postharvest Diseases of Pome Fruits," *Phytopathology*, 81(10):1175–1176 (1991). (Abstract No. 309).

Janisiewicz, W. J., et al., "Antagonism of *Sporobolomyces Roseus* against Major Postharvest Pathogens of Apple and Pear," *Phytopathology* 81:1214 (1991). (Abstract No. 606).

Janisiewicz, W. J., et al., "Biological Control of Postharvest Diseases of Pears with *Psuedomonas syringae pv. lachrymans*," *Phytopathology* 79:1216 (1989). (Abstract No. 645).

Janisiewicz, W. J., "Population Dynamics of Two Biological Control Agents on Apple and Their Compatibility with Postharvest Treatments," *Phytopathology* 77:1777 (1987) (Abstract No. 723).

Janisiewicz, W. J. et al., "Biocontrol of Blue Mold and Gray Mold and Survival of Biocontrol Agent on Various Pear Cultivars in Storage," *Phytopathology* 80(7):671 (1990) (Abstract).

Janisiewicz, W. J., "Biological Control of Diseases of Fruits," K. J. Mukerji and K. L. Gary (Ed.), *Biocontrol of Plant Diseases* vol. 2, pp. 153–165, (CRC Press, Boca Raton, 1988).

Janisiewicz, W. J., "Control of Postharvest Diseases of Fruits with Biocontrol Agents," *ASPAC Food & Fertilizer Technology Center, Technical Bulletin* 125:1–13 (1991).

Janisiewicz, W. J., "Biocontrol of Postharvest Diseases of Apples with Antagonist Mixtures," *Phytopathology* 78(2):194–198 (1988).

Janisiewicz, W. J., "Biological Control of Postharvest Fruit Diseases," *Handbook of Applied Mycology* vol. 1, pp. 301–326 (1991).

Janisiewicz, W. J. et al., "Biological Control of Postharvest Diseases of Pome Fruits," pp. 49–59, Biological Control of Postharvest Disease of Fruits and Vegetables, Workshop Proceedings, USDA, ARS–92, (Jun. 1991) pp. 49–59.

Hirano, S. S., et al., "Population Biology and Epidemiology of *Pseudomonas syringae*," *Annu. Rev. Phytopathol.* 28:155–177 (1990).

Denny, T. P., "Differentiation of *Pseudomonas syringae pv. tomato* from *P. s. Syringae* with a DNA Hybridization Probe," *Phytopathology* 78(19):1186–1193 (1988).

Denny, T. P., "Genetic Diversity and Relationships of Two Pathovars of *Pseudomonas syringae*," *J. General Microbiology* 134:1949–1960 (1988).

Roberts, R. G., "Postharvest Biological Control of Gray Mold of Apple by *Cryptococcus laurentii*," *Phytopathology* 80(6):526–530 (1990).

Roberts, R. G., "Characterization of Postharvest Biological Control of Deciduous Fruit Diseases by *Cryptococcus s/pp.*," pp. 37–48, Biological Control of Postharvest Diseases of Fruits and Vegetables, Workshop Proceedings (1991).

Sugar, D., et al., "Effects of Fruit Nutrient Management and Postharvest Yeast Application on Fungal Decay in Pear," *Phytopathology* 81(10):1163 (1991).

Sugar, D., et al., "Integration of Cultural and Biological Methods for Control of Postharvest Decay in Pear," *Phytopathology* 82:1076 (1992) (Abstract No. A115).

Shefelbine, P. A., et al., "Population Dynamics of *Cryptococcus laurentii* in Wounds in Apple and Pear Fruit Stored Under Ambient or Controlled Atmospheric Conditions," *Phytopathology* 80:1020 (1990) (Abstract No. A497).

(List continued on next page.)

Primary Examiner—Michael G. Wityshyn
Assistant Examiner—Kristin Larson
Attorney, Agent, or Firm—Hamilton, Brook, Smith & Reynolds, P.C.

[57] ABSTRACT

A biologically pure culture of *Pseudomonas syringae* having the identifying characteristics of the deposited strain designated as ATCC 55389 is disclosed. A composition for inhibiting microbial decay on fruit is disclosed, the composition including a strain of *Pseudomonas syringae* having the identifying characteristics of the deposited strain designated as ATCC 55389 and a carrier. The composition has a concentration of the strain in the carrier which is sufficient to significantly inhibit microbial decay on the fruit. Additionally, a method for inhibiting microbial decay on fruit is disclosed including the step of exposing the fruit to a composition which includes a sufficient concentration of a strain of *Pseudomonas syringae* having the characteristics of the deposited strain as ATCC 55389 to significantly inhibit microbial decay.

44 Claims, 2 Drawing Sheets

OTHER PUBLICATIONS

Stack, J. P., et al., "Biocontrol of Blue Mold of Apple under Common and Controlled Atmosphere Storage," *Phytopathology* 82(10):1063 (1992) (Abstract A5).

Chalutz, E. et al., "Postharvest Biocontrol of Green and Blue Mold and Sour Rot of Citrus Fruit by *Debaryomyces hansenii*," *Plant Disease* 74(2):134–137 (1990).

Pusey, P. L. et al., "Postharvest Biological Control of Stone Fruit Brown Rot by *Bacillus subtilis*," *Plant Disease* 68(9):753–756 (1984).

Smilanick, J. L. et al., "Control of Green Mold of Lemons with *Pseudomonas* Species," *Plant Disease* 76(5):481–485 (1992).

Wilson, C. L. et al., "Biological Control of Rhizopus Rot of Peach with *Enterobacter cloacae*," *Phytopathology* 77 (2):303–305 (1987).

Wilson, C. L. et al., "Postharvest Biological Control of *Penicillium* Rots of Citrus with Antagonistic Yeasts and Bacteria," *Sci. Hortic.* 40:105–112 (1989).

McLaughlin, R. J. et al., "Biological Control of Postharvst Diseases of Grape, Peach, and Apple with Yeasts *Kloeckera apiculata* and *Candida guilliermondii*," *Plant Disease* 76(5):470–473 (1992).

Roberts, R. G., "Biological Control of Mucor Rot of Pear by *Crytococcus laurenti, C. flavus,* and *C. albidus*," *Phytopathology* 80:1051 (1990) (Abstract).

```
Lane A - Size Marker
Lane B - Pseudomonas syringae pv. lachrymans
Lane C - Pseudomonas syringae pv. mori
Lane D - Pseudomonas syringae pv. tagetis
Lane E - Pseudomonas syringae ESC-10
Lane F - Pseudomonas syringae ESC-11
Lane G - Pseudomonas syringae ESC-11
```

```
Lane A - Size Marker
Lane B - Pseudomonas syringae pv. lachrymans
Lane C - Pseudomonas syringae pv. tagetis
Lane D - Pseudomonas syringae pv. mori
Lane E - Pseudomonas syringae ESC-10
Lane F - Pseudomonas syringae ESC-11
Lane G - Pseudomonas syringae ESC-11
```

PSEUDOMONAS SYRINGAE ATCC 55389 AND USE THEREOF FOR INHIBITING MICROBIAL DECAY ON FRUIT

BACKGROUND OF THE INVENTION

Many fruits suffer from postharvest diseases that are caused by pathogens, such as fungi, that can cause rot as well as other forms of decay during postharvest handling and storage. Often, infection by pathogens is initiated through injuries made at harvest through cut stems, etc. or through mechanical wounds to the surface of the fruit during handling. This decay on harvested fruit causes substantial economic losses to the fruit industry each year.

Pome and citrus fruits are examples of fruits that are vulnerable to infection by postharvest diseases. These diseases include blue mold, gray mold, green mold, sour rot and mucor rot. Such molds are often present on the fruits at harvest and grow during storage and shipping to cause severe decay.

Past attempts to control postharvest diseases have included treating fruits with chemicals. However, many chemicals that have been in long-time use are now ineffective due to the increasing number of chemical-resistant strains of pathogens associated with postharvest diseases. Further, many chemicals have been recently recognized as potentially hazardous to humans and the environment.

Biological control of postharvest diseases is an alternative to chemical control. However, few biocontrol products are commercially available. There is a need for biological agents that are safe for humans and the environment.

SUMMARY OF THE INVENTION

The present invention relates to a biologically pure culture of a strain of *Pseudomonas syringae* having the characteristics of the deposited strain designated as American Type Culture Collection (ATCC) 55389. It also relates to a composition for inhibiting the microbial decay of fruit, the composition including a strain of *Pseudomonas syringae* having the characteristics of the deposited strain designated as ATCC 55389 and a carrier. The composition has a concentration of the strain in the carrier which is sufficient to significantly inhibit microbial decay of the fruit. Additionally, the invention includes a method for inhibiting microbial decay of fruit including the step of exposing the fruit to a composition which includes a sufficient concentration of a strain of *Pseudomonas syringae* having the characteristics of the deposited strain as ATCC 55389 to significantly inhibit microbial decay.

This invention has many advantages. For example, *Pseudomonas syringae* ATCC 55389 occurs naturally and grows well under conditions typically encountered in postharvest storage of fruit. The composition, which includes the bacterium, is easy to apply to the surface of fruit and is safe to handle. Also, this strain of *Pseudomonas syringae* exhibits good survival and growth under conditions, such as temperature, humidity, and natural or modified atmospheres that are typically encountered during postharvest treatment and storage of fruit. Further, this strain of *Pseudomonas syringae* colonizes wound surfaces very effectively.

DETAILED DESCRIPTION OF THE INVENTION

Figure 1:
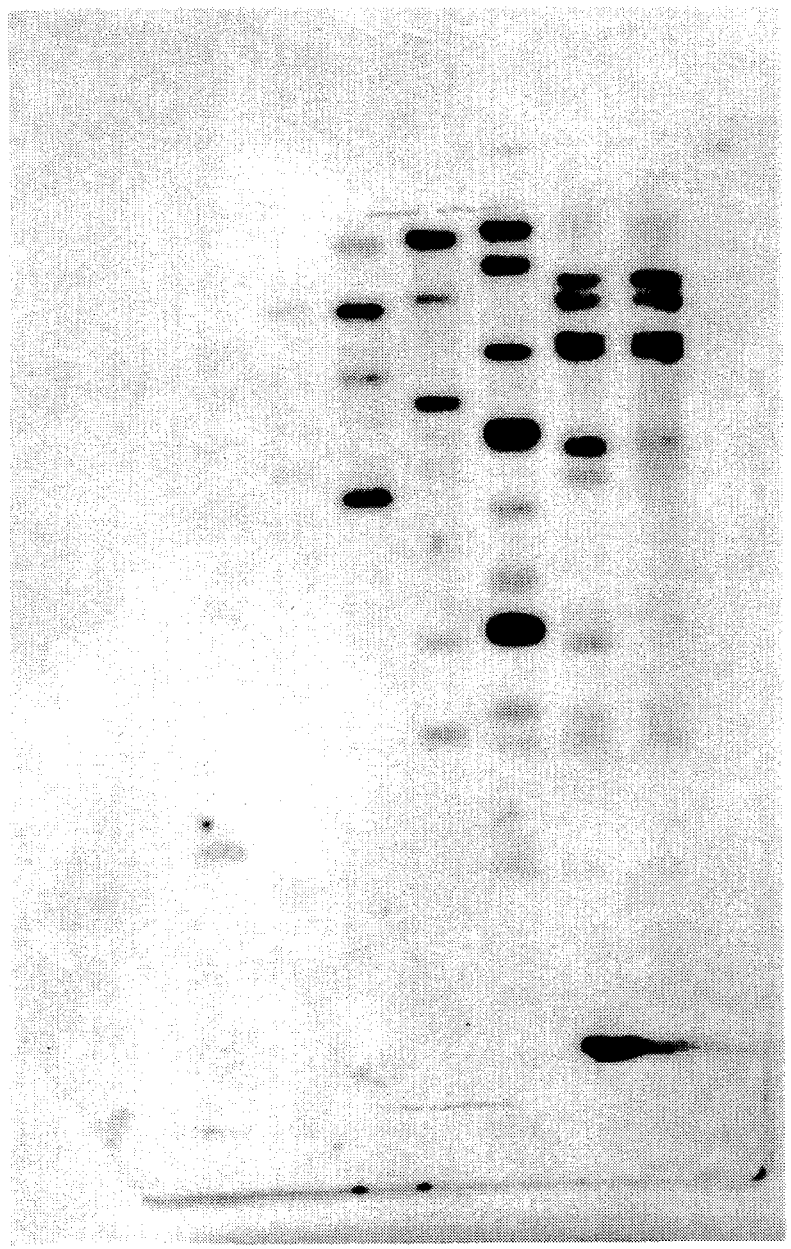
FIG. 1 illustrates an electrophoretogram of Restriction Fragment Length Polymorphism data of genomic DNA from *Pseudomonas syringae* ATCC 55389 and a series of comparison test samples that were digested with EcoRV using six probes cloned from *Pseudomonas syringae* ESC-10.
Figure 2:
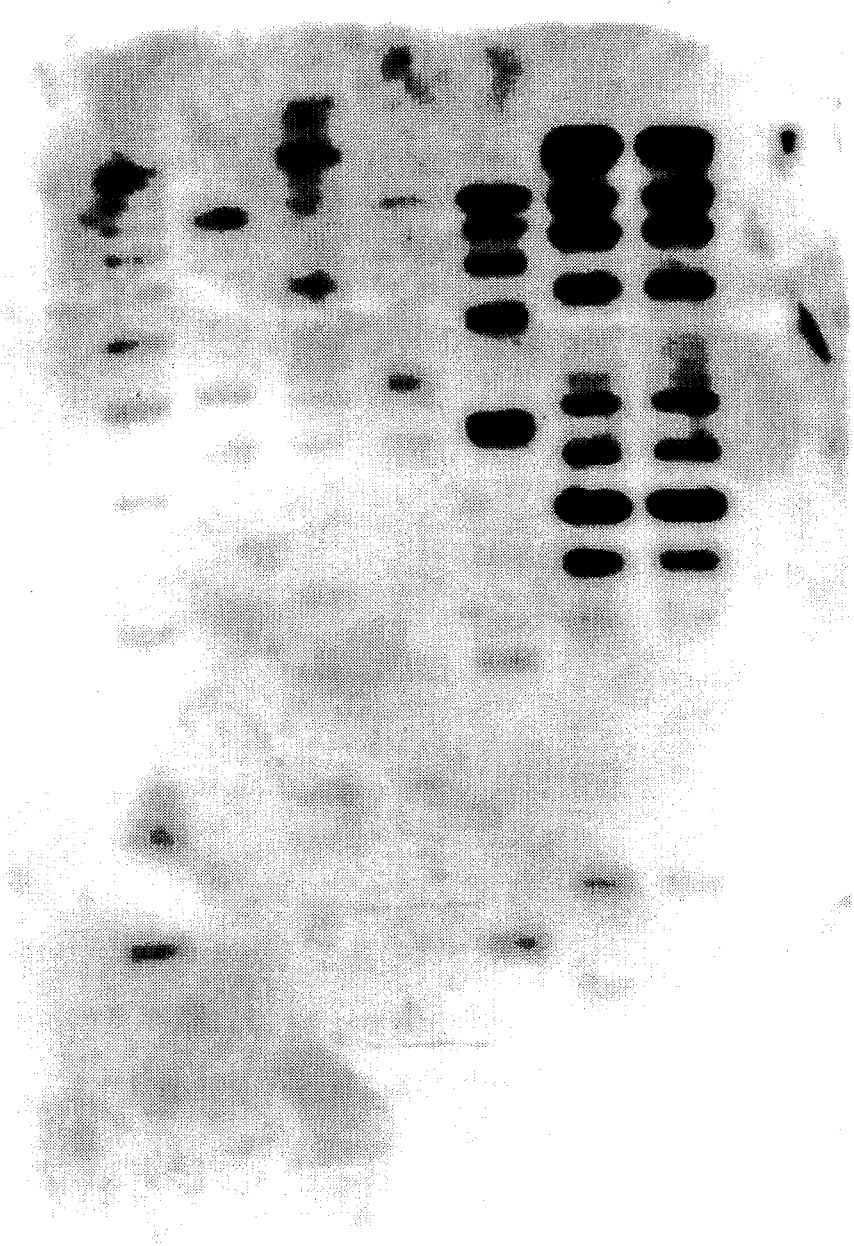
FIG. 2 illustrates an electrophoretogram of Restriction Fragment Length Polymorphism data of genomic DNA from *Pseudomonas syringae* ATCC 55389 and a series of comparison test samples distinguishing *Pseudomonas syringae* isolates using twelve probes cloned from *Pseudomonas syringae* ESC-11.

The above features and other details of the biologically pure culture, composition and method of this invention for controlling the microbial decay of postharvest fruits will now be more particularly described with relationship to the accompanying figures and pointed out in the claims. It will be understood that the particular embodiments of the invention are shown by way of illustration and not as limitations of the invention. The principal feature of this invention can be employed in various embodiments without departing from the scope of the invention. All parts and percentages are by weight unless otherwise specified.

The novel strain of *Pseudomonas syringae* described herein can be applied to pome fruits to eliminate or reduce postharvest rot. Pome fruits typically have a fleshy outer layer and a central core with seeds, which are enclosed in a capsule. Examples of pome fruits include apples, pears, pomegranate, quince and the like. Particularly preferred apples include Golden Delicious, Red Delicious, Granny Smith, Empire and Macintosh. Other fruits can also be treated, of course, including but not limited to citrus fruits, such as oranges, grapefruit, lemons, limes and the like.

Postharvest diseases which commonly infect pome fruits include blue mold (*Penicillium expansum*), gray mold (*Botrytis cinerea*), and mucor rot (*Mucor piriformis*). The postharvest diseases for citrus fruits include blue mold (*Penicillium italicum*), green mold (*Penicillium digitatum*), and sour rot (*Geotrichum candidum*). Often, infection is initiated at injuries made at harvest or by mechanical wounds to the surface of the fruit during postharvest handling.

*Pseudomonas syringae* ATCC 55389 bacterium was isolated by EcoScience Corp. as isolate ESC-10 (hereinafter "ESC-10"). Viable cultures of the strain were deposited on Jan. 29, 1993 with the culture collection at the American Type Culture Collection, 12301 Parklawn Drive, Rockville, Md., under the accession number ATCC 55389.

ESC-10 is cultured in a suitable liquid medium on a shaker flask. Alternatively, the bacterium can be cultured in a fermentation vessel. The bacterium is plated and cultured in a nutritionally-rich medium that is sufficient to support the growth of the organism. A preferred medium includes nutrient-yeast extract-dextrose broth. The bacterium is cultured under aerobic conditions at a suitable temperature, such as a temperature in the range of between about 1° and 28° C. The preferred temperature is in the range of between about 25° and 28° C. The preferred pH of the nutrient medium is in the range of between about six and eight. The period of incubation required for the bacterium to reach a stationary phase is generally between about 16 and 20 hours.

The cultured bacterium is harvested, such as by centrifugation or filtration, and then stored at a suitable temperature, such as a temperature of about 4° C. Thereafter, the bacterium can be combined with a suitable carrier to form a composition. The carrier can be an aqueous medium, such as water or a 0.85% NaCl solution, or a non-aqueous medium, such as a lipid-based oil or wax. In addition, the carrier can be a dry powder. In one embodiment, the dry carrier is either a clay or talc. To determine the number of colony forming units (cfu), seven ten-fold dilutions are carried out. Ten μl of the three highest dilutions are plated on nutrient agar to determine the cfus. The plates are incubated at 25° C. for 48 hours before counting.

The bacterium includes identifying characteristics that distinguish it from other strains of *Pseudomonas syringae*. One identifying characteristic is its resultant electrophoretogram of Restriction Fragment Length Polymorphism (RFLP) data. The bacterium has been distinguished, for example, from two other strains of *Pseudomonas syringae* isolated by Dr. Wojciech J. Janisiewicz of the United States Department of Agriculture Appalachian Fruit Research Station in Kearneysville, W. Va. as *Pseudomonas syringae* PL3 (hereinafter "PL3") and *Pseudomonas syringae* L-59-66 (hereinafter "L-59-66"). *Pseudomonas syringae* ESC-11 (hereinafter "ESC-11"), is a subculture of L-59-66 isolated by EcoScience Corp. of Worcester, Mass. Viable cultures of ESC-11 have been deposited with the culture collection at the Northern Regional Research Center, U.S. Department of Agriculture, Peoria, Ill. 61604, under the accession number NRRL 18739. PL3, L-59-66 and ESC-11 are used as comparison samples to ESC-10. Another distinguishing and identifying characteristic of ESC-10 is its value of similarity to other strains of *Pseudomonas syringae* as described below by fatty acid analysis. An additional identifying characteristic is the efficacy of a concentration of an ESC-10 suspension in significantly inhibiting microbial decay on fruit and in preventing postharvest fruit diseases; it is superior to other strains of equal concentration of *Pseudomonas syringae*, such as PL3 and ESC-11.

DNA polymorphisms are detected by employing standard methods of molecular biology using DNA probes that were cloned from ESC-10 or ESC-11. The genomic DNA from cells of ESC-10 is isolated by standard techniques, such as Miller et al., *Nucleic Acids Research*, 16:1215 (1988) or using a commercially available kit, such as BIO G Nome™ from BIO 101 of La Jolla, Calif. The DNA is then cleaved into fragments by an EcoRI or BamHI restriction enzyme from the genome of *Pseudomonas syringae* PL3 as disclosed by Sambrook et al., *Molecular Cloning, A Laboratory Manual*, 2d. ed., Cold Spring Harbor Press, Cold Spring Harbor, N.Y. (1989). The cleaved DNA is then disposed on the top surface of a gel of agarose or polyacrylamide and electrophoresed. An electric current is passed through the gel, and each fragment moves through the gel at a rate that depends on the logarithm of its molecular weight. The movement of the fragments produces a series of bands. Each band corresponds to a collection of DNA fragments. The length of a particular fragment is determined by calibrating the gel with a control, DNA fragments of known links. The cleaved DNA is then transferred to and immobilized on a nylon membrane using Southern blotting methods, Sambrook et al. The cloned DNA probes are non-radioactively labelled by using a Genius™ detection kit from Boehringer Mannheim. The probes are hybridized to the Southern blot and detected. The probes detect specific DNA bands, DNA fragments, in the genome that correspond to the probe sequence. When these sequences occur on different size or length restriction fragments, the resulting pattern difference is called a Restriction Fragment Length Polymorphism (RFLP) that distinguishes particular isolates and is considered a type of a DNA fingerprint.

FIG. 1 discloses an electrophoretogram of RFLP data for a comparison among ESC-10, *Pseudomonas syringae* ESC-11 and a series of comparison test samples of a Restriction Fragment Length Polymorphism of genomic DNA that were digested with EcoRV using a mixture of six probes, pESI10-50, pESI10-53, pESI10-54, pESI10-55, pESI10-56, and pESI10-60, cloned from ESC-10. These isolates were also compared to *Pseudomonas syringae* pv. *lachrymans* ATCC 11965, Pseudomonas syringae pv. *mori* ATCC 19872, and *Pseudomonas syringae* pv. *tagetis* ATCC 43127. In Lanes A–G, left to right, the RFLPs are Lane A, a size marker; Lane B, *Pseudomonas syringae* pv. *lachrymans* ATCC 11965; Lane C, *Pseudomonas syringae* pv. *mori* ATCC 19872; Lane D, *Pseudomonas syringae* pv. *tagetis* ATCC 43127; Lane E, ESC-10; and Lanes F and G, ESC-11 (replicate samples). About ten bands are visible in ESC-10 and three of them are similar in size and possibly DNA sequence with ESC-11 which has eleven visible bands. The ATCC isolates 11965, 19872 and 43127 all have fewer bands and distinctive fingerprints indicating that ESC-10 and ESC-11 each differ from the three ATCC isolates that were judged to be similar based on fatty acid analysis conducted by Microcheck, Inc., which is discussed below. The weak signals of pathovars *Pseudomonas syringae* pv. *lachrymans* ATCC 11965 and *Pseudomonas syringae* pv. *mori* ATCC 19872 suggest that little of the probe DNA is homologous to the genomes of pathovars *lachrymans* and *mori*. *Pseudomonas syringae* pv. *tagetis* has only two restriction fragments in common with ESC-10 and ESC-11.

FIG. 2 further discloses results of a comparison among ESC-10, *Pseudomonas syringae* ESC-11 and a series of comparison test samples of a Restriction Fragment Length Polymorphism of genomic DNA that were digested with EcoRV using a mixture of twelve probes, pPUB1 through pPUB12, cloned from ESC-11. These isolates were also compared to *Pseudomonas syringae* pv. *lachrymans* ATCC 11965, *Pseudomonas syringae* pv. *mori* ATCC 19872 and *Pseudomonas syringae* pv. *tagetis* ATCC 43127. In Lanes A–G, left to right, the RFLPs are Lane A, a size marker; Lane B, *Pseudomonas syringae* pv. *lachrymans* ATCC 11965; Lane C, *Pseudomonas syringae* pv. *tagetis* ATCC 43127; Lane D, *Pseudomonas syringae* pv. *mori* ATCC 19872; Lane E, ESC-10; and Lanes F and G, ESC-11 (replicate samples). At least eleven bands are visualized for isolate ESC-11, while only seven bands are visible for ESC-10. At least six bands of ESC-10 are different from ESC-11. The three ATCC isolates show fewer bands and distinct fingerprints. The weak signals of pathovars *Pseudomonas syringae* pv. *lachrymans* and *Pseudomonas syringae* pv. *mori* suggest that little of the probe DNA is homologous to the genome of pathovars *lachrymans* and *mori*. *Pseudomonas syringae* pv. *tagetis* has only two genomes in common with ESC-10 and ESC-11. The ESC-10 and ESC-11 are readily distinguished from each other and from the three other isolates judged to be similar based on fatty acid analysis conducted by Microcheck, Inc., which is discussed below.

ESC-10 was identified taxonomically by Microcheck, Inc., Northfield, Vt. using fatty acid analysis of cells grown in trypticase soy broth agar culture. The following values of similarity index were obtained:

| | |
|---|---|
| *Pseudomonas syringae* | 0.946 |
| *P. syringae* pv. mori ATCC 19872 | 0.943 |
| *P. syringae* pv. lachrymans ATCC 11965 | 0.889 |
| *P. syringae* pv. viridiflava | 0.876 |
| *P. syringae* pv. cichorii | 0.855 |
| *Chromobacterium violaceum* | 0.550 |

Colonies of the bacterium exhibit a cream color on nutrient agar.

The invention generally includes a method and a composition for significantly inhibiting microbial decay on fruits. The method includes exposing the fruit to a composition which includes a sufficient concentration of a strain of *Pseudomonas syringae* having the identifying characteristics of the deposited strain designated as ATCC 55389 to significantly inhibit microbial decay. The composition includes a strain of *Pseudomonas syringae* having the identifying characteristics of the deposited strain designated as ATCC 55389 and a carrier. The strain has a concentration which is sufficient to significantly inhibit microbial decay of the fruit.

The concentration of the *Pseudomonas syringae* is sufficient to significantly inhibit microbial decay on fruits, which is understood to be a concentration of *Pseudomonas syringae* that causes an observable decrease in decay as compared to decay on an inoculated untreated control of sample fruit. Inhibition is observed by measuring disease severity, which is the size of the lesion (i.e. amount of decay), and disease incidence, which is the number of fruits or wounds with lesions. An example of this is seen in Table 1, which displays Golden Delicious apples inoculated with blue mold (*Penicillium expansum*) and treated with various types of *Pseudomonas syringae* or left untreated (i.e. *Penicillium expansum* control). Both the disease severity and disease incidence are considered to be significantly inhibited by treatment with ESC-10 (0 mm, 0%) compared to the uninoculated control (12 mm, 53%), the untreated *Penicillium expansum* control (30 mm, 100%), and the treatment with other isolates of *Pseudomonas syringae*, PL3 (26 mm, 100%), ESC-11 (25 mm, 100%) and L-59-66 (28 mm, 100%). In one embodiment, ESC-10 has a concentration in an aqueous suspension of the composition in the range of between about $10^2$ cfu/ml and $10^{10}$ cfu/ml. In a preferred embodiment, ESC-10 has a concentration in the range of between about $10^6$ cfu/ml and $10^9$ cfu/ml.

More than one component that can inhibit microbial decay can be included in the composition to control the microbial decay on fruits by the method of the invention. For example, *Pseudomonas syringae* ESC-10 can be combined with a second microbial component, such as *Sporobolomyces roseus* or Cryptococcus spp., which can be effective against microbial decay in fruit. Alternatively, ESC-10 can be combined with a chemical, such as a fungicide, thiabendazole, which can be effective against microbial decay in fruit.

The composition is then applied to the surface of the fruit by a suitable technique. Examples of suitable techniques include spraying, drenching, dipping or brushing. The treatments are applied after harvest and prior to storage or during storage or after storage in preparation for shipping.

The composition can be included in a formula which has additional components to further treat the fruit. The formula can contain additives to further increase the effectiveness of the application of the composition. Examples of suitable additives include surfactants, antioxidants, and fruit coatings. Further, the formula can be applied in a coating to cover the fruit to provide for certain physical and aesthetic fruit appearances. The formula can include a fruit coating, such as a wax, a shellac or Nature Seal™ food coating from EcoScience Corp. Nature Seal™ coating is a liquid coating made from food grade ingredients primarily to control the ripening of various produce commodities. An example of one embodiment includes a polysaccharide polymer, a preservative, an acidulant, lecithin and an emulsifier. The formula can be in the form of a liquid, granules, or a powder. The formula can be applied directly to the fruit as a concentrate or it can be diluted with water or other suitable liquid.

The following are examples of various embodiments of the method and the composition for inhibiting the microbial decay on fruits.

EXAMPLE 1

Natural microbial fruit populations were collected from the surface of fruits, twigs and leaves and plated onto various media including nutrient agar. Fungus, yeast, and bacterium isolates were screened for antagonistic properties against postharvest pathogenic isolates using bioassays with apples and citrus that measure mean lesion diameter and percentage protection.

Postharvest pathogens of apples and citrus fruit were obtained from fruit surfaces and from ATCC and other culture collections. The pathogen isolates of *Botrytis cinerea, Penicillium expansum,* and *Mucor piriformis* were tested to determine pathogenicity on apples and pears; isolates of *Penicillium digitatum, Penicillium italicum,* and *Geotrichum candidum* were tested for pathogenicity on citrus fruit. The pathogens *Botrytis cinerea* and *Penicillium expansum* were challenged with potential antagonists on apples and pears, and *Penicillium italicum, Penicillium digitatum,* and *Geotrichum candidum* were challenged with the potential antagonists on citrus fruit.

Yeast, bacterium, and fungus isolates exhibiting 100% protection of apple fruit against *Botrytis cinerea Penicillium expansum,* and *Mucor piriformis* were further evaluated for efficacy to determine at what concentration they maintained their antagonist characteristics. Several concentrations of potential antagonists of about $10^5$, $10^6$, $10^7$, $10^8$, $10^9$ and $10^{10}$ colony forming units/ml were compared. Disease severity and lesion diameter and disease incidence (percentage infection) were measured. Similarly, the same isolates (i.e. those exhibiting 100% protection) were challenged with *Penicillium italicum, Penicillium digitatum,* and *Geotrichum candidum* on Valencia oranges. Disease severity and disease incidence were measured. The isolates that showed the greatest protection of the fruit from decay were selected for further study.

This screening led to the selection of the bacterium isolate ESC-10 for continued study and registration. ESC-10 was isolated from a young shoot tip collected from an apple tree in an unmanaged orchard in Belchertown, Mass. This shoot tip was brought back to the laboratory and stored at a temperature of about 4° C. until the isolation was performed twenty-three days later. The shoot tip was added to a test tube containing 10–20 ml Acidified Yeast Malt broth. The test tube was incubated at 23° C. for 48 hrs. Isolations to L Agar and King's Medium B were made from the growth that occurred in the test tube.

The following general procedure was employed to produce concentrated ESC-10. A flask containing a suitable volume of yeast extract-dextrose broth (YDB) or nutrient-yeast extract-dextrose broth (NYDB) was inoculated with cells of ESC-10 from a nutrient agar plate. Flasks or tubes were placed on a shaker for about 18–24 hrs. The resulting suspension of actively-growing cells was centrifuged into a pellet (5–10 minutes at 7,000–9,000 rpm, depending on the volume of suspension), and the supernatant was discarded. Pelleted cells were washed twice in sterile 0.85% NaCl buffer (saline), sterile distilled water (SDW), or sterile tap water (STW) and then resuspended in the same solution as that used for washing. ESC-10 was usually tested at concentrations in the range $10^7$ to $10^9$ cfu/ml. These concentrations were prepared by resuspending washed cells in a volume of saline, SDW, or STW equal to the original volume in which cells were grown and then diluting this suspension by a ratio of 1:10 or 1:100. Alternatively, a spectrophotometer was used to prepare a concentration of $10^8$ cfu/ml by the following method: Concentrated, washed cells in SDW were added to SDW until a suspension with 50% transmittance at 550 nm was achieved. A similar procedure was followed to prepare concentrations of other isolates of *Pseudomonas syringae*, i.e., ESC-11, L-59-66, and PL3.

EXAMPLE 2

Golden Delicious apples were obtained from commercial orchards or fruit distributors. The apples were harvested at a maturity stage appropriate for storage and held at 1° C. for less than three months before use in bioassays.

The pathogen for blue mold, *Penicillium expansum*, was isolated from decayed apples after a few months in storage. The isolate produced large lesions when inoculated to untreated apples. The fungus was maintained on potato dextrose agar (PDA). The inocula consisting of aqueous conidial suspensions of $2 \times 10^4$ conidia per milliliter were prepared from 7–14 day old cultures of *Penicillium expansum*. The aqueous suspension was formed with sterile deionized water.

The antagonistic bacterium, *Pseudomonas syringae* ESC-10 was prepared by the method described above in Example 1.

At treatment, apples were wounded three times around the equator. Wounds were made by puncturing the fruit with a blunt, metal tool that was 3 mm long and 2 mm in diameter. Wounds were inoculated with 10 μl of saline or STW, pathogen spores ($10^4$ conidia/ml), or a mixture of antagonist cells ($10^7$ cfu/ml) and pathogen spores ($10^4$ conidia/ml). Antagonist cells from four isolates of *Pseudomonas syringae* (ESC-10, ESC-11, PL3 and L-59-66) were individually tested in combination with the pathogen (*Penicillium expansum*). Five replicate apples were used for each treatment. Treated apples were placed on fruit trays in plastic boxes, and the boxes were placed at 25° C. for seven days. The percentage of wounds with lesions (disease incidence) was determined and the average diameter of lesions (disease severity) was calculated for each treatment.

TABLE 1

Bioassay Using Sterile Tap Water As Diluent; Golden Delicious Apples

| Treatment | Disease Incidence (%) | Disease Severity (mm) |
|---|---|---|
| Sterile tap water | 53 | 12 |
| *P. expansum* | 100 | 30 |
| P.e. + ESC-10 | 0 | 0 |
| P.e. + PL3 | 100 | 26 |
| P.e. + ESC-11 | 100 | 25 |
| P.e. + L-59-66 | 100 | 28 |
| Concentrations: | | |
| *P. expansum* | $2 \times 10^4$ conidia/ml | |
| ESC-10 | <$10^7$ cfu/ml | |
| PL3 | <$10^7$ cfu/ml | |
| ESC-11 | <$10^7$ cfu/ml | |
| L-59-66 | $3 \times 10^7$ cfu/ml | |

In Table 1, the lesion development on the wounded Golden Delicious apples that were treated with ESC-10 and challenged with *Penicillium expansum* is shown. Treatment of the wounded apples with ESC-10 completely prevented disease development (incidence and severity) from *Penicillium expansum*. In contrast, the control apples that were treated with sterile water having no *Penicillium expansum* had an incidence of disease of 53% and 12 mm lesions. Apples treated with only *Penicillium expansum* had an incidence of disease of 100% and lesions of 30 mm. The apples treated with *Penicillium expansum* and the other strains of *Pseudomonas syringae* (PL3, ESC-11 and L-59-66) all had disease incidences of 100% and lesions of 26, 25 and 28 mm, respectfully. Disease incidence and disease severity were significantly less with ESC-10 than with the control or the other *Pseudomonas syringae* strains.

EXAMPLE 3

The same procedure was followed as in Example 2 except the diluent to form the aqueous suspension was 0.85%, by weight, NaCl buffer instead of sterile tap water.

TABLE 2

Bioassay Using 0.85% NaCl Buffer As Diluent; Golden Delicious Apples

| Treatment | Disease Incidence (%) | Disease Severity (mm) |
|---|---|---|
| 0.85% NaCl | 40 | 8 |
| *P. expansum* | 100 | 25 |
| P.e. + ESC-10 | 27 | 3 |
| P.e. + PL3 | 100 | 26 |
| P.e. + ESC-11 | 100 | 26 |
| P.e. + L-59-66 | 100 | 24 |
| Concentrations: | | |
| *P. expansum* | $2 \times 10^4$ conidia/ml | |
| ESC-10 | $4 \times 10^9$ cfu/ml | |
| PL3 | $2 \times 10^9$ cfu/ml | |
| ESC-11 | $2 \times 10^9$ cfu/ml | |
| L-59-66 | $6 \times 10^8$ cfu/ml | |

In Table 2, the lesion development on the wounded Golden Delicious apples that were inoculated and treated with *Pseudomonas syringae* ESC-10 and other isolates of *Pseudomonas syringae* is shown. Treatment of wounded apples with ESC-10 resulted in an incidence of disease of 27% and average lesion size of 3 mm. In contrast, the control apples, which were treated with a 0.85% NaCl aqueous solution having no *Penicillium expansum*, had an incidence of disease of 40% and average lesion size of 8 mm. Apples treated with only *Penicillium expansum* in the 0.85% NaCl diluent had an incidence of disease of 100% and lesions of 25 mm. The apples treated with *Penicillium expansum* and the other strains of *Pseudomonas syringae* PL3, ESC-11 and L-59-66 in the 0.85% NaCl diluent all had disease incidences of 100% and lesions of 26, 26 and 24 mm, respectively. Disease incidence and disease severity were significantly less with ESC-10.

EXAMPLE 4

The same procedure was followed as in Example 2 except four diluents were used to prepare aqueous suspensions with sterile distilled water, sterile tap water, 0.085% NaCl buffer, by weight, and 0.85% NaCl buffer. The pathogen in each case was *Penicillium expansum*. Three strains of *Pseudomonas syringae*, ESC-10, PL3 and L-59-66, were tested. As shown in Table 3 for all four diluents, the suspensions of ESC-10 significantly inhibited disease from *Penicillium expansum*. ESC-10 had disease incidences in the range zero to seventeen percent and lesions in the range of from zero to two millimeters. In comparison, the *Penicillium expansum* control had a disease incidence of 100% in each case except one and disease severity of from 25 to 32 mm, while PL3 and L-59-66 had disease incidences of 100% in each case and severity ranged from 26 to 29 mm.

TABLE 3

Bioassay Using Four Diluents;
Golden Delicious Apples 0.85% NaCl buffer as diluent:

| Treatment | Disease Incidence (%) | Disease Severity (mm) |
|---|---|---|
| P. expansum | 100 | 32 |
| P.e. + ESC-10 | 0 | 0 |
| P.e. + PL3 | 100 | 28 |
| P.e. + L-59-66 | 100 | 28 |

Concentrations:

| P. expansum | $2 \times 10^4$ conidia/ml |
|---|---|
| ESC-10 | $3 \times 10^9$ cfu/ml |
| PL3 | $2 \times 10^8$ cfu/ml |
| L-59-66 | $4 \times 10^9$ cfu/ml |

0.085% NaCl buffer as diluent:

| Treatment | Disease Incidence (%) | Disease Severity (mm) |
|---|---|---|
| P. expansum | 92 | 25 |
| P.e. + ESC-10 | 8 | 1 |
| P.e. + PL3 | 100 | 29 |
| P.e. + L-59-66 | 100 | 26 |

Concentrations:

| P. expansum | $2 \times 10^4$ conidia/ml |
|---|---|
| ESC-10 | $5 \times 10^9$ cfu/ml |
| PL3 | $8 \times 10^8$ cfu/ml |
| L-59-66 | $2 \times 10^9$ cfu/ml |

Sterile distilled water as diluent:

| Treatment | Disease Incidence (%) | Disease Severity (mm) |
|---|---|---|
| P. expansum | 100 | 29 |
| P.e. + ESC-10 | 17 | 2 |
| P.e. + PL3 | 100 | 29 |
| P.e. + L-59-66 | 100 | 28 |

Concentrations:

| P. expansum | $2 \times 10^4$ conidia/ml |
|---|---|
| ESC-10 | $4 \times 10^9$ cfu/ml |
| PL3 | $8 \times 10^8$ cfu/ml |
| L-59-66 | $3 \times 10^9$ cfu/ml |

Sterile tap water as diluent:

| Treatment | Disease Incidence (%) | Disease Severity (mm) |
|---|---|---|
| P. expansum | 100 | 32 |
| P.e. + ESC-10 | 0 | 0 |
| P.e. + PL3 | 100 | 27 |
| P.e. + L-59-66 | 100 | 29 |

Concentrations:

| P. expansum | $2 \times 10^4$ conidia/ml |
|---|---|
| ESC-10 | $<10^5$ cfu/ml |
| PL3 | $<10^5$ cfu/ml |
| L-59-66 | $<10^5$ cfu/ml |

EXAMPLE 5

The same procedure was followed as in Example 3 except that Red Delicious Apples were used. Five apples, with three wounds per apple, were used for each treatment. The three treatments were sterile 0.85% NaCl buffer without *Penicillium expansum*, sterile 0.85% NaCl buffer with *Penicillium expansum* ($2 \times 10^4$ conidia/ml), and sterile 0.85% NaCl buffer containing a mixture of *Penicillium expansum* ($2 \times 10^4$ conidia/ml) and ESC-10 ($9 \times 10^8$ cfu/ml).

TABLE 4

Bioassay of ESC-10 on Red Delicious Apples

| | 7 DAYS | | 14 DAYS | |
|---|---|---|---|---|
| Treatment | Disease Incidence (%) | Disease Severity (mm) | Disease Incidence (%) | Disease Severity (mm) |
| 0.85% NaCl | 7 | 1 | 7 | 2 |
| P. expansum | 100 | 18 | 100 | 43 |
| P.e. + ESC-10 | 0 | 0 | 0 | 0 |

Concentration:

| P. expansum | $2 \times 10^4$ conidia/ml |
|---|---|
| ESC-10 | $9 \times 10^8$ cfu/ml |

As shown in Table 4, after fourteen days, apples treated with water alone had a disease incidence of 7% and an average lesion diameter of 2 mm. Apples treated with *Penicillium expansum* were 100% diseased and had an average lesion diameter of 43 mm. Apples treated with the mixture of *Penicillium expansum* and ESC-10 had no disease.

EXAMPLE 6

The same procedure, as in Example 5, was followed except Granny Smith Apples were used instead of Red Delicious Apples. As shown in Table 5, similar results were attained with ESC-10 by significantly preventing blue mold disease caused by *Penicillium expansum*.

TABLE 5

Bioassay of ESC-10 on Granny Smith Apples

| | 7 DAYS | | 14 DAYS | |
|---|---|---|---|---|
| Treatment | Disease Incidence (%) | Disease Severity (mm) | Disease Incidence (%) | Disease Severity (mm) |
| 0.85% NaCl | 0 | 0 | 7 | 2 |
| P. expansum | 100 | 29 | 100 | 62 |
| P.e. + ESC-10 | 7 | 1 | 27 | 3 |

Concentrations:

| P. expansum | $2 \times 10^4$ conidia/ml |
|---|---|
| ESC-10 | $9 \times 10^8$ cfu/ml |

Apples treated with the 0.85% NaCl buffer only after fourteen days had minimal disease whereas those treated with a suspension of *Penicillium expansum* were 100% diseased and had an average lesion diameter of 62 mm. Apples treated with a mixture of *Penicillium expansum* and ESC-10 also had minimal disease incidence. ESC-10 was effective at reducing disease development caused by *Penicillium expansum*.

EXAMPLE 7

Similar procedures to those followed in Examples 4–6 were followed except that both organically and non-organically grown Golden Delicious apples were used. Both types of apples were treated with five treatments: 0.85% NaCl buffer (control), *Penicillium expansum* alone, a mixture of *P. expansum* and ESC-10, a mixture of *P. expansum* and PL3, and a mixture of *P. expansum* and ESC-11. All treatment suspensions were prepared with 0.85% NaCl buffer.

TABLE 6

Comparison of ESC-10, PL3, and ESC-11 on Organically and Non-Organically Grown Golden Delicious Apples Organically Grown Apples

| | Disease Incidence (%) | Disease Severity (mm) |
|---|---|---|
| 0.85% NaCl | 42 | 9 |
| P. expansum | 100 | 29 |
| P. expansum + ESC-10 | 0 | 0 |
| P. expansum + PL3 | 100 | 27 |
| P. expansum + ESC-11 | 100 | 26 |

Non-Organically Grown Apples

| | Disease Incidence (%) | Disease Severity (mm) |
|---|---|---|
| 0.85% NaCl | 58 | 12 |
| P. expansum | 100 | 26 |
| P. expansum + ESC-10 | 0 | 0 |
| P. expansum + PL3 | 100 | 27 |
| P. expansum + ESC-11 | 100 | 28 |

Concentrations:

| | |
|---|---|
| P. expansum | $2 \times 10^4$ conidia/ml |
| ESC-10 | $2 \times 10^9$ cfu/ml |
| PL3 | $2 \times 10^7$ cfu/ml |
| ESC-11 | $3 \times 10^9$ cfu/ml |

On both the organically and non-organically grown apples, ESC-10 prevented disease development completely whereas PL3 and ESC-11 had essentially no effect on disease development.

EXAMPLE 8

Procedures similar to those in previous Examples 2–7 were followed except that the pathogen *Botrytis cinerea* was used in addition to *Penicillium expansum*. Golden Delicious apples were wounded and then inoculated with the seven treatments listed in Table 7. These treatments were: sterile distilled water (control), *P. expansum* alone, *B. cinerea* alone, a mixture of *P. expansum* and *B. cinerea*, a mixture of ESC-10 and *P. expansum*, a mixture of ESC-10 and *B. cinerea*, and a mixture of ESC-10 and both pathogens (*P. expansum* and *B. cinerea*). Five apples, each with five wounds around the equator, were used for each treatment. Treated fruit were placed in plastic boxes and stored at 22° C. for 7 days.

TABLE 7

Bioassay of ESC-10 against *Penicillium expansum* and *Botrytis cinerea* on Golden Delicious Apples

| Treatment | Disease Incidence (%) | Disease Severity (mm) |
|---|---|---|
| Water | 0 | 0 |
| P. expansum | 100 | 24 |
| B. cinerea | 96 | 38 |
| P. expansum + B. cinerea | 100 | 31 |
| P. expansum + ESC-10 | 0 | 0 |
| B. cinerea + ESC-10 | 4 | 1 |
| P. expansum + B. cinerea + | 16 | 2 |

TABLE 7-continued

Bioassay of ESC-10 against *Penicillium expansum* and *Botrytis cinerea* on Golden Delicious Apples

ESC-10

Concentrations:

| | |
|---|---|
| P. expansum | $2 \times 10^4$ conidia/ml |
| B. cinerea | $2 \times 10^4$ conidia/ml |
| ESC-10 | $1 \times 10^9$ cfu/ml |

As shown in Table 7, ESC-10 was essentially effective at preventing *P. expansum* and *B. cinerea* from causing disease. When ESC-10 was used against the pathogens individually, it essentially prevented disease development at wounds inoculated with *P. expansum* and allowed only one small lesion to develop at the 25 wounds inoculated with *B. cinerea* (4%). When ESC-10 was used against the mixture of pathogens, lesions developed at only 16% of the wounds, and the average lesion diameter, 2 mm, was much less than on apples inoculated with the pathogen combination and no ESC-10 (31 mm).

EXAMPLE 9

Golden Delicious apples were obtained from a commercial orchard, where standard cultural practices were followed, and were treated immediately after harvest. Suspension of antagonists, *Pseudomonas syringae* isolates ESC-10 and ESC-11, were prepared following the methods described above in Example 1.

Three pathogens, *Penicillium expansum*, *Botrytis cinerea*, and *Mucor piriformis*, were maintained and grown following the methods described above in Example 2. *M. piriformis* causes the disease Mucor rot on stored apples and pears. The isolate of *M. piriformis* used was isolated from a diseased apple and caused large lesions when inoculated into wounds on untreated apples and pears.

Just before treatment, apples were wounded twice around the equator, on opposite sides, with a blunt, metal tool, which was 3 mm long and 2 mm in diameter. Five replicates were used for each treatment; each replicate consisted of 20 wounded fruit. The pathogens were used only as a mixture containing equal concentrations of each of the three species, *P. expansum*, *B. cinerea*, and *M. piriformis*. There were three treatments: the pathogen mixture, ESC-10 mixed with the pathogens, and ESC-11 mixed with the pathogens. The concentrations of pathogens were $1 \times 10^3$ conidia/ml, and the concentrations of antagonists were $3 \times 10^8$ cfu/ml for ESC-10 and $7 \times 10^7$ cfu/ml for ESC-11. All treatment suspensions were prepared with non-sterile tap water. Treatments were applied by dipping 20 wounded fruit at a time in a suspension and agitating the fruit vigorously to ensure thorough coverage of all apples. Treated apples were placed on fruit trays, and the trays were placed in cardboard boxes. Boxes were placed in a refrigerated cold room at 2°–4° C. for 11 weeks. Immediately after all apples were treated, the experiment was repeated, and these boxes of treated apples were placed in a commercial, refrigerated controlled atmosphere (CA) storage room, at 1°–2° C. and approximately 1% $O_2$ and 3% $CO_2$, for 16 weeks. Treatments were evaluated by measuring disease incidence as the percentage of fruit that developed lesions.

TABLE 8

Efficacy of ESC-10 against a Mixture of
*Penicillium expansum, Botrytis cinerea*, and
*Mucor piriformis* on Golden Delicious Apples at
Two Storage Regimes

| Treatment | Disease Incidence (%)* | |
|---|---|---|
| | Cold Storage | Controlled Atmosphere Storage |
| Pathogens | 100 a | 99 a |
| Pathogens + ESC-11 | 78 b | 87 b |
| Pathogens + ESC-10 | 51 c | 57 c |
| Concentrations: | | |
| Pathogens | $1 \times 10^3$ conidia/ml | |
| ESC-10 | $3 \times 10^8$ cfu/ml | |
| ESC-11 | $7 \times 10^7$ cfu/ml | |

*Treatment means were separated by Fisher's Protected Least Significance Difference (LSD), P = 0.05

As shown in Table 8, ESC-10 was significantly better than ESC-11 at preventing diseases caused by *P. expansum, B. cinerea*, and *M. piriformis* both in regular cold storage and in controlled atmosphere storage. ESC-10 protected 49% (100-51) and 43% (100-57) of the apples from infection in cold and CA storage, respectively, under conditions very conducive to disease development, which resulted in 99–100% disease in the unprotected pathogens treatment.

EXAMPLE 10

A procedure similar to that described in Example 9 was followed except that Red Delicious apples were used instead of Golden Delicious apples and that the apples were stored only in controlled atmosphere storage. Three treatments were used: a mixture of three pathogens, *Penicillium expansum, Botrytis cinerea*, and *Mucor piriformis*, ESC-10 mixed with the pathogens, and ESC-11 mixed with the pathogens. The concentrations of pathogens were $1 \times 10^3$ conidia/ml, and the concentrations of antagonists were $3 \times 10^8$ cfu/ml for ESC-10 and $3 \times 10^8$ cfu/ml for ESC-11. All treatment suspensions were prepared with non-sterile tap water containing the antioxidant diphenylamine (DPA) at 1,000 parts per million (ppm). Boxes of treated apples were stored in a commercial, refrigerated controlled atmosphere (CA) storage room, at 1°–2° C. and approximately 1% $O_2$ and 3% $CO_2$ for 16 weeks.

TABLE 9

Efficacy of ESC-10 against a Mixture of
*Penicillium expansum, Botrytis cinerea*, and
*Mucor piriformis* on Red Delicious Apples in
Controlled Atmosphere Storage

| Treatment | Disease Incidence (%)* |
|---|---|
| Pathogens | 99 a |
| Pathogens + ESC-11 | 78 b |
| Pathogens + ESC-10 | 62 c |
| Concentrations: | |
| Pathogens | $1 \times 10^3$ conidia/ml |
| ESC-10 | $3 \times 10^8$ cfu/ml |
| ESC-11 | $3 \times 10^8$ cfu/ml |

*Treatment means were separated by Fisher's Protected Least Significance Difference (LSD), P = 0.05

As shown in Table 9, both ESC-10 and ESC-11 were effective at preventing postharvest diseases caused by *P. expansum, B. cinerea*, and *M. piriformis* on Red Delicious apples in controlled atmosphere storage. Although disease control by ESC-10 and ESC-11 was not significantly different, treatment with ESC-10 resulted in a lower disease incidence. ESC-10 protected 38% of the apples from infection and ESC-11 protected 22% of the apples under conditions very conducive to disease development, which resulted in 99% disease on apples treated with pathogens alone.

EXAMPLE 11

A procedure similar to that described in Examples 9 and 10 was followed except that d'Anjou pears were used instead of apples, only two pathogens (*Penicillium expansum* and *Botrytis cinerea*) were used, and pears were stored only in refrigerated cold storage. Four treatments were compared: The mixture of two pathogens (*Penicillium expansum* and *Botrytis cinerea*), ESC-10 mixed with the pathogens, ESC-11 mixed with the pathogens, and the fungicide thiabendazole mixed with the pathogens. The concentrations of pathogens were $1 \times 10^3$ spores/ml and of antagonists were approximately $1 \times 10^8$ cfu/ml for ESC-10 and ESC-11. The rate of thiabendazole was equivalent to the recommended commercial rate (i.e., 16 fluid ounces of a 42.3% flowable formulation in 100 gallons of water, or 1.25 ml per liter). All treatment suspensions were prepared with non-sterile tap water. Boxes of treated pears were stored in a refrigerated cold room at 2°–4° C. for 4 and 13 weeks.

TABLE 10

Efficacy of ESC-10 Against a Mixture of
*Penicillium expansum* and *Botrytis cinerea* on
d'Anjou Pears in Refrigerated Cold Storage

| Treatment | Disease Incidence (%)* | |
|---|---|---|
| | 4 weeks | 13 weeks |
| Pathogens | 94 a | 100 a |
| Thiabendazole | 56 b | 91 ab |
| Pathogens + ESC-10 | 50 bc | 79 b |
| Pathogens + ESC-11 | 7 d | 39 c |
| Concentrations: | | |
| Pathogens | $1 \times 10^3$ conidia/ml | |
| Thiabendazole | 570 ppm | |
| ESC-10 | $1 \times 10^8$ cfu/ml | |
| ESC-11 | $1 \times 10^8$ cfu/ml | |

*Treatment means were separated by Fisher's Protected Least Significance Difference (LSD), P = 0.05

As shown in Table 10, both ESC-10 and ESC-11 were effective at preventing postharvest diseases cause by *P. expansum* and *B. cinerea* on d'Anjou pears in cold storage. Although disease control by ESC-11 was significantly better than all other treatments at both 4 and 13 weeks, control by ESC-10 was similar to (i.e., not significantly different from) that by the fungicide thiabendazole, which currently is the industry standard.

EXAMPLE 12

Valencia oranges were obtained from commercial groves using standard cultivation practices.

The pathogens, *Penicillium italicum* and *Penicillium digitatum*, were isolated from decayed oranges. The isolates produced large lesions when inoculated into wounds on untreated oranges. The fungi were maintained on PDA. The inocula consisting of aqueous conidial suspensions of 1×10⁵ conidia per milliliter were prepared from 7–14 day old cultures of *Penicillium italicum* and *Penicillium digitatum*. The antagonistic bacterium, ESC-10 was isolated and maintained by the method described above in Example 1.

Just before treatment, oranges were wounded five times around the equator with a blunt, metal tool that was 3 mm long and 2 mm in diameter. Wounds were inoculated with 10 μl of treatment suspensions. There were five treatments: water alone (control), *Penicillium digitatum* (1×10⁵ conidia/ml), a mixture of *P. digitatum* (1×10⁵ conidia/ml) and ESC-10 (7×10⁹ cfu/ml), *Penicillium italicum* (1×10⁵ conidia/ml), and a mixture of *P. italicum* (1×10⁵ conidia/ml) and ESC-10 (7×10⁹ cfu/ml). Five replicate fruit were used for each treatment. Treated oranges were placed on fruit trays in plastic boxes, and boxes were held at 22° C. for 6 days. At the end of six days, two measures of disease incidence were recorded for each treatment: the percentage of fruit with lesions and the percentage of wounds with lesions.

TABLE 11

Bioassay of ESC-10 on Valencia Oranges

| Treatment | Disease Incidence (%) | |
|---|---|---|
| | Fruit | Wounds |
| Water | 0 | 0 |
| *P. italicum* | 80 | 40 |
| *P. italicum* + ESC-10 | 40 | 8 |
| *P. digitatum* | 100 | 96 |
| *P. digitatum* + ESC-10 | 60 | 28 |

Concentrations:

| | |
|---|---|
| *P. italicum* | 1 × 10⁵ conidia/ml |
| *P. digitatum* | 1 × 10⁵ conidia/ml |
| ESC-10 | 7 × 10⁹ cfu/ml |

As shown in Table 11, disease incidence caused by both species of Penicillium was significantly less when fruit were treated with ESC-10. Disease incidence from *Penicillium italicum* was 50% less (80 v. 40) on the fruit and 80% less (40 v. 8) around the wounds. Disease incidence from *Penicillium digitatum* was 40% less (100 v. 60) on the fruit and 71% less (96 v. 28) around the wounds.

EXAMPLE 13

The same procedure was followed as in Example 12 except lemons were used instead of oranges.

TABLE 12

Bioassay of ESC-10 on Lemons

| Treatment | Disease Incidence (%) | |
|---|---|---|
| | Fruit | Wounds |
| Water | 0 | 0 |
| *P. italicum* | 100 | 100 |
| *P. italicum* + ESC-10 | 60 | 24 |
| *P. digitatum* | 100 | 100 |
| *P. digitatum* + ESC-10 | 0 | 0 |

Concentrations:

| | |
|---|---|
| *P. italicum* | 1 × 10⁵ conidia/ml |
| *P. digitatum* | 1 × 10⁵ conidia/ml |
| ESC-10 | 7 × 10⁹ cfu/ml |

As shown in Table 12, disease incidence caused by both species of Penicillium was significantly less when fruit were treated with ESC-10. Disease incidence from *Penicillium italicum* was 40% less (100 v. 60) on the fruit and 76% less (100 v. 24) around the wounds. Disease from *Penicillium digitatum* was significantly inhibited by ESC-10.

EXAMPLE 14

Lemons were inoculated with *Penicillium digitatum* and *Penicillium italicum* in combination with ESC-10 by the same method of Example 13. ESC-10 had a concentration of 3×10⁹ cfu/ml *Penicillium digitatum* and *Penicillium italicum* both had concentrations of 2×10⁴ cfu/ml. Five lemons with four wounds per lemon were used for each treatment. The inoculated lemons were stored at 22° C. for seven days.

TABLE 13

Bioassay of ESC-10 on Lemons

| Treatment | Disease Incidence (%) | |
|---|---|---|
| | Fruit | Wounds |
| Water | 80 | 65 |
| *P. digitatum* | 100 | 100 |
| *P. digitatum* + ESC-10 | 20 | 5 |
| *P. italicum* | 100 | 100 |
| *P. italicum* + ESC-10 | 0 | 0 |

Concentrations:

| | |
|---|---|
| *P. digitatum* | 2 × 10⁴ condia/ml |
| *P. italicum* | 2 × 10⁴ condia/ml |
| ESC-10 | 3 × 10⁹ cfu/ml |

As shown in Table 13, disease incidences caused by both species of Penicillium was significantly less when fruit were treated with ESC-10. Disease incidence from *Penicillium digitatum* was 80% less (100 v. 20) on the fruit and 95% less (100 v. 5) around the wounds. Disease from Penicillium italicum was significantly inhibited by ESC-10.

EXAMPLE 15

Lemons were inoculated with the pathogens, *Penicillium digitatum* and *Penicillium italicum*, with methods similar to those in Examples 12–14 except that a 0.85% NaCl buffer was used to prepare inoculum suspensions and two types of wounds were used. Lemons received either a puncture wound, which was 2 mm deep and 2 mm in diameter, or a slash wound, which was 5 mm long, 1 mm wide, and 2 mm deep. The concentration of ESC-10 was 4×10⁹ cfu/ml, and the concentrations of the pathogens were 2×10⁴ conidia/ml. Five lemons, each with four wounds around the equator, were used for each wound type/treatment combination. Lemons were inoculated by dipping for 2 minutes in treatment suspensions. Treatments were 0.85% NaCl buffer (control), *P. digitatum* alone, *P. italicum* alone, *P. digitatum* mixed with ESC-10, and *P. italicum* mixed with ESC-10. The inoculated lemons were placed in plastic boxes and stored at 22° C. for 8 days.

TABLE 14

Bioassay of Lemons with Puncture and Slash Wounds

| Treatment | Wound Type | Disease Incidence (%) Fruit | Wounds |
|---|---|---|---|
| 0.85% NaCl | Puncture | 100 | 100 |
|  | Slash | 100 | 100 |
| P. digitatum | Puncture | 100 | 100 |
|  | Slash | 100 | 100 |
| P. italicum | Puncture | 100 | 100 |
|  | Slash | 100 | 100 |
| ESC-10 + P. digitatum | Puncture | 40 | 40 |
|  | Slash | 20 | 20 |
| ESC-10 + P. italicum | Puncture | 20 | 20 |
|  | Slash | 20 | 5 |

Concentrations:

| ESC-10 | $4 \times 10^9$ cfu/ml |
|---|---|
| P. digitatum | $2 \times 10^4$ conidia/ml |
| P. italicum | $2 \times 10^4$ conidia/ml |

As shown in Table 14, with both types of wounds, punctures and slashes, ESC-10 was effective at preventing the incidence of lesions, particularly in slash type wounds, as compared to the 0.85% NaCl buffer control or unchallenged *Penicillium digitatum* and *Penicillium italicum*.

EXAMPLE 16

Marsh Ruby Red grapefruits were obtained from a commercial packing house within 72 hours after harvest. Grapefruits had received no postharvest chemical applications prior to treatment. ESC-10 was prepared following the methods described above in Example 1.

Three pathogens, *Penicillium digitatum, Penicillium italicum,* and *Geotrichum candidum,* were maintained and grown following the methods described above in Example 12. *G. candidum* causes the disease sour rot on stored citrus fruit. The isolate of *G. candidum* used was isolated from a diseased grapefruit and caused large lesions when inoculated into wounds on untreated citrus fruits.

Just before treatment, the grapefruits were wounded twice around the equator, on opposite sides, with a sharp, metal tool that was 3 mm long and 3 mm in diameter. Ten replicate grapefruits were used for each treatment. There were eight treatments: water (control), ESC-10 alone, *P. digitatum* alone, *P. digitatum* mixed with ESC-10, *P. italicum* alone, *P. italicum* mixed with ESC-10, *G. candidum* alone, and *G. candidum* mixed with ESC-10. Concentrations of pathogens were approximately $1 \times 10^4$ conidia/ml, and the concentration of ESC-10 was $5 \times 10^8$ cfu/ml. Treated grapefruits were placed in cardboard boxes. Boxes containing grapefruits inoculated with Penicillium were stored at 12° C. for 22 days; boxes containing grapefruits inoculated with *G. candidum* were stored at 12° C. for 14 days and then at 22° C. for 8 days. Treatments were evaluated by measuring disease incidence as the percentage of fruit that developed lesions.

TABLE 15

Efficacy of ESC-10 against *Penicillium digitatum, Penicillium italicum,* and *Geotrichum candidum* on Marsh Ruby Red Grapefruits

| Treatment | Disease Incidence (%) |
|---|---|
| Water | 40 |
| ESC-10 | 0 |
| P. digitatum | 80 |
| P. digitatum + ESC-10 | 5 |
| P. italicum | 90 |
| P. italicum + ESC-10 | 30 |
| G. candidum | 38 |
| G. candidum + ESC-10 | 8 |

Concentrations:

| Pathogens | approximately $1 \times 10^4$ conidia/ml |
|---|---|
| ESC-10 | $5 \times 10^8$ cfu/ml |

As shown in Table 15, ESC-10 was very effective at inhibiting disease on grapefruits caused by all three pathogens. Green mold was 94% less (80 v. 5); blue mold was 67% less (90 v. 30); and sour rot was 79% less (38 v. 8). ESC-10 essentially inhibited disease development from naturally occurring inoculum that resulted in a disease incidence of 40% on grapefruits in the water control treatment.

EXAMPLE 17

A procedure similar to that described in Example 16 was followed except that Valencia oranges were used instead of grapefruits, ESC-10 was applied at 0, 6, or 12 hours after pathogen inoculation, and two types of wounds were used. Oranges were wounded twice around the equator, on opposite sides. One wound was 3 mm deep and 3 mm in diameter and the other wound was 3 mm deep and 1 mm in diameter. Five replicates were used for each treatment, and each replicate consisted of ten wounded oranges. There were 13 treatments: Water (control); ESC-10 alone; a mixture of *P. digitatum* and *P. italicum* (i.e., Penicillium); Penicillium and ESC-10; Penicillium with ESC-10 added 6 hours later; Penicillium with ESC-10 added 12 hours later; Penicillium with the fungicide thiabendazole at 1,000 ppm added 12 hours later; Penicillium with a mixture of ESC-10 and the fungicide thiabendazole at 20 ppm added 12 hours later; *G. candidum; G. candidum* mixed with ESC-10; *G. candidum* with ESC-10 added 6 hours later; *G. candidum* with ESC-10 added 12 hours later; and *G. candidum* with the fungicide thiabendazole at 1,000 ppm added 12 hours later. Concentrations of pathogens were $1 \times 10^4$ conidia/ml and the concentration of ESC-10 was $5 \times 10^8$ cfu/ml. Treated oranges were placed in cardboard boxes. Boxes containing oranges inoculated with Penicillium were stored at 12° C. for 15 days; boxes containing oranges inoculated with *G. candidum* were stored at 22° C. for 15 days.

TABLE 16

Efficacy of ESC-10 Against *Penicillium digitatum, Penicillium italicum,* and *Geotrichum candidum* on Valencia Oranges

| | Disease Incidence (%) | |
|---|---|---|
| Treatment | 3 mm Wounds | 1 mm Wounds |
| Water | 6 ab | 4 ab |
| ESC-10 | 0 a | 0 a |
| P. digitatum + P. italicum | 90 e | 92 f |
| Penicillium + ESC-10 | 38 c | 14 bc |
| Penicillium + ESC-10 at 6 hr. | 64 d | 22 cd |
| Penicillium + ESC-10 at 12 hr. | 34 c | 48 e |
| Penicillium + 1,000 ppm | 14 b | 48 e |

TABLE 16-continued

Efficacy of ESC-10 Against *Penicillium digitatum*, *Penicillium italicum*, and *Geotrichum candidum* on Valencia Oranges

| | | |
|---|---|---|
| thiabendazole at 12 hr. | | |
| Penicillium + [ESC-10 + 20 ppm thiabendazole] at 12 hr. | 6 ab | 30 d |
| *G. candidum* | 14 b | 12 abc |
| *G. candidum* + ESC-10 | 6 ab | 4 ab |
| *G. candidum* + ESC-10 at 6 hr. | 6 ab | 2 ab |
| *G. candidum* + ESC-10 at 12 hr. | 0 a | 8 ab |
| *G. candidum* + 1,000 ppm thiabendazole at 12 hr. | 2 a | 26 cd |

Concentrations:

| | |
|---|---|
| *P. digitatum* | $1 \times 10^4$ conidia/ml |
| *P. italicum* | $1 \times 10^4$ conidia/ml |
| *G. candidum* | $1 \times 10^4$ conidia/ml |
| ESC-10 | $5 \times 10^8$ cfu/ml |

*Treatment means were separated by Fisher's Protected Least Significance Difference (LSD), P = 0.05

As shown in Table 16, ESC-10 was very effective at preventing disease caused by *P. digitatum* and *P. italicum* in both 3 mm and 1 mm diameter wounds. All treatments with ESC-10, including those added 6 and 12 hours after the pathogen, resulted in significantly less disease than in the Penicillium treatment (*P. digitatum*+*P. italicum*) without ESC-10. The efficacy observed with ESC-10 was applied hours after the Penicillium pathogens suggests the ability to prevent the further development of an already initiated disease condition. In addition, a combination of ESC-10 and a reduced rate of thiabendazole applied to 1 mm wounds 12 hours after pathogen inoculation was more effective at preventing disease than was either of the two ingredients alone. The effects of ESC-10 on the incidence of sour rot caused by *Geotrichum candidum* were not statistically significant in most cases presumably because of lower infection. However, all treatment with ESC-10 appear to have reduced disease incidence compared to treatment with *Geotrichum candidum* only.

Equivalents

Those skilled in the art will recognize, or be able to ascertain using no more than routine experimentation, many equivalents to the specific embodiments of the invention described specifically herein. Such equivalents are intended to be encompassed in the scope of the claims.

I claim:

1. A biologically pure culture of a strain of *Pseudomonas syringae* having all the identifying characteristics of the deposited strain *P. syringae* ATCC 55389.

2. A composition for application to fruit to inhibit the microbial decay of fruit, comprising a strain of *Pseudomonas syringae* having all the identifying characteristics of the deposited strain *P. syringae* ATCC 55389, and a carrier, said strain having a concentration which is sufficient to inhibit microbial decay of the fruit.

3. The composition of claim 2 wherein said strain is Pseudomonas ATCC 55389.

4. A method for inhibiting microbial decay of fruit comprising the step of exposing the fruit to a composition which comprises a sufficient concentration of a strain of *Pseudomonas syringae* having all the identifying characteristics of the deposited strain *P. syringae* ATCC 55389 to inhibit microbial decay.

5. The method of claim 4 wherein said strain is Pseudomonas ATCC 55389.

6. The method of claim 4 wherein the fruit comprises pome fruit.

7. A method of claim 6 wherein the pome fruit comprises apples.

8. The method of claim 7 wherein the apples comprise Golden Delicious apples.

9. The method of claim 7 wherein the apples comprise Red Delicious apples.

10. The method of claim 7 wherein the apples comprise Granny Smith apples.

11. The method of claim 6 wherein the pome fruit comprises pears.

12. The method of claim 11 wherein the pears comprise d'Anjou pears.

13. The method of claim 4 wherein the fruit comprises citrus fruit.

14. The method of claim 13 wherein the citrus fruit comprises oranges.

15. The method of claim 13 wherein the citrus fruit comprises lemons.

16. The method of claim 13 wherein the citrus fruit comprises grapefruit.

17. The method of claim 4 wherein the microbial decay is blue mold.

18. The method of claim 17 wherein the blue mold is caused by *Penicillium expansum* or *Penicillium italicum.*

19. The method of claim 4 wherein the microbial decay is gray mold.

20. The method of claim 19 wherein the gray mold is caused by *Botrytis cinerea.*

21. The method of claim 4 wherein the microbial decay is mucor rot.

22. The method of claim 21 wherein the mucor rot is caused by *Mucor piriformis.*

23. The method of claim 4 wherein the microbial decay is green mold.

24. The method of claim 23 wherein the green mold is *Penicillium digitatum.*

25. The method of claim 4 wherein the microbial decay is sour rot.

26. The method of claim 25 wherein the sour rot is caused by *Geotrichum candidum.*

27. The method of claim 4 wherein the concentration of *Pseudomonas syringae* is in the range of between $10^6$ to $10^9$ cfu per milliliter.

28. The method of claim 4 wherein the composition is an aqueous suspension.

29. The method of claim 4 wherein the composition further comprises a food coating.

30. The method of claim 29 wherein the food coating is Nature Seal™.

31. The method of claim 4 wherein the composition further comprises a fungicide.

32. The method of claim 31 wherein the fungicide is thiabendazole.

33. A method for inhibiting the microbial decay of fruit, comprising the steps of:

a) forming a composition by culturing a strain of *Pseudomonas syringae* bacterium having all the identifying characteristics of the deposited strain *P. syringae* ATCC 55389 and by suspending the cultured strain of *Pseudomonas syringae* in an aqueous medium to form a composition having a sufficient concentration of the strain of *Pseudomonas syringae* to inhibit the microbial decay of fruit; and b) applying the composition to the surface of the fruit in an amount sufficient to inhibit microbial decay of fruit.

34. The method of claim 33 wherein the fruit is citrus fruit.

35. The method of claim 34 wherein the citrus fruit comprises oranges.

36. The method of claim 34 wherein the citrus fruit comprises lemons.

37. The method of claim 34 wherein the citrus fruit comprises grapefruit.

38. The method of claim 33 wherein the fruit is pome fruit.

39. The method of claim 38 wherein the pome fruit is apples.

40. The method of claim 39 wherein the apples comprise Golden Delicious apples.

41. The method of claim 39 wherein the apples comprise Granny Smith apples.

42. The method of claim 39 wherein the apples comprise Red Delicious apples.

43. The method of claim 30 wherein the pome fruit is pears.

44. The method of claim 43 wherein the pears comprise d'Anjou Pears.

* * * * *

UNITED STATES PATENT AND TRADEMARK OFFICE
CERTIFICATE OF CORRECTION

PATENT NO. : 5,554,368
DATED : September 10, 1996
INVENTOR(S) : James P. Stack, Steven N. Jeffers, Baruch Sneh and Teresa S. Wright It is certified that error appears in the above-indentified patent and that said Letters Patent is hereby corrected as shown below:

In Column 22, line 7: After the word "of", delete "claim 30" and insert therefor --claim 38--.

Signed and Sealed this

Thirty-first Day of December, 1996

Attest:

BRUCE LEHMAN

Attesting Officer     Commissioner of Patents and Trademarks